(12) United States Patent
Overmyer et al.

(10) Patent No.: US 10,143,514 B2
(45) Date of Patent: Dec. 4, 2018

(54) ELECTRONIC BAILOUT FOR MOTORIZED RF DEVICE

(71) Applicant: Ethicon Endo-Surgery, LLC, Guaynabo, PR (US)

(72) Inventors: Mark D. Overmyer, Cincinnati, OH (US); Rudolph H. Nobis, Mason, OH (US); Aaron C. Voegele, Loveland, OH (US); Catherine A. Corbett, Cincinnati, OH (US); David C. Yates, West Chester, OH (US); Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 405 days.

(21) Appl. No.: 14/940,430

(22) Filed: Nov. 13, 2015

(65) Prior Publication Data

US 2017/0135711 A1    May 18, 2017

(51) Int. Cl.
| | | |
|---|---|---|
| *A61B 17/295* | (2006.01) | |
| *A61B 17/285* | (2006.01) | |
| *A61B 18/14* | (2006.01) | |
| *A61B 17/00* | (2006.01) | |
| *A61B 90/00* | (2016.01) | |
| *A61B 18/00* | (2006.01) | |

(52) U.S. Cl.
CPC ............ *A61B 18/1445* (2013.01); *A61B 2017/00353* (2013.01); *A61B 2017/00398* (2013.01); *A61B 2017/00734* (2013.01); *A61B 2018/00607* (2013.01); *A61B 2018/1455* (2013.01); *A61B 2090/08021* (2016.02)

(58) Field of Classification Search
CPC ........... A61B 2090/08021; A61B 2017/00353; A61B 2017/320094; A61B 2017/320093; A61B 2017/00398; A61B 2017/00734; A61B 18/1445; A61B 17/320092; A61B 2018/1455; A61B 2018/00607; A61B 17/285; A61B 17/29; A61B 17/295; A61B 18/1442; A61B 18/1447; A61B 2018/1452
See application file for complete search history.

(56) References Cited

U.S. PATENT DOCUMENTS

2009/0202387 A1    8/2009   Dlugos, Jr. et al.
2014/0367446 A1*  12/2014   Ingmanson ........ A61B 17/07207
                                                  227/175.2

* cited by examiner

*Primary Examiner* — Eric Rosen
*Assistant Examiner* — Mikail Mannan
(74) *Attorney, Agent, or Firm* — Mintz Levin Cohn Ferris Glovsky and Popeo, P.C.

(57) ABSTRACT

Methods and devices are provided for retracting a cutting assembly in the event of a failure on a motorized electrosurgical device. For instance, a surgical device is provided that includes a handle portion with an elongated shaft having first and second jaws. The device includes a cutting assembly configured to cut tissue engaged between the first and second jaws. A motor is included to drive the cutting assembly, and a processor is coupled to the motor. An actuator on the device is configured to receive an input from a user that causes power to be supplied to the motor. The device has a normal mode in which the processor controls the motor, and the device has a bailout mode in which the processor is bypassed and power is delivered directly to the motor.

18 Claims, 5 Drawing Sheets

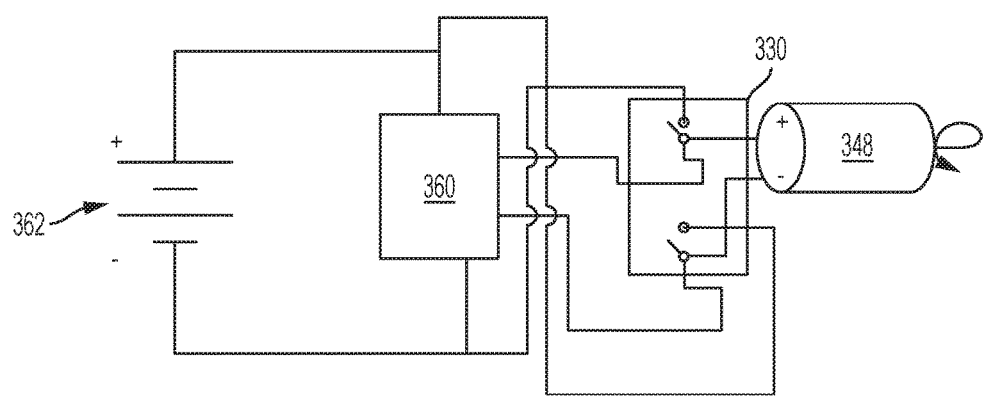
FIG. 7
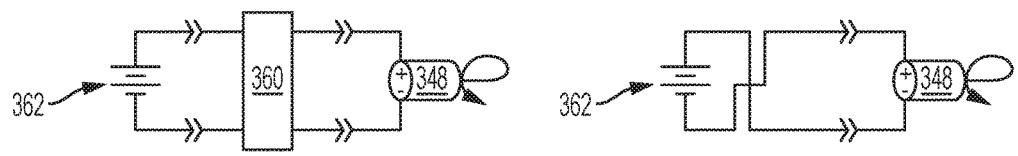
FIG. 8
FIG. 9

ELECTRONIC BAILOUT FOR MOTORIZED RF DEVICE

FIELD

Methods and devices are provided for retracting a cutting assembly in the event of a failure on a motorized electrosurgical device.

BACKGROUND

Endoscopic surgical instruments are often preferred over traditional open surgical devices since a smaller incision associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, stapler, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. With powered devices, any problems that occur may prevent removal of the device through the access port. For example, in the event the end effector becomes jammed during a firing stroke or the device otherwise fails, the end effector cannot be removed because tissue is engaged between the jaws. The surgeon may be forced to open up the patient and cut the instrument out of the patient, potentially causing serious harm to the patient.

Accordingly, methods and devices are needed to allow for removal of an instrument even upon failure of the instrument, especially retraction of any mechanisms that prevent the jaws of an end effector from opening and releasing clamped tissue.

SUMMARY

Various methods and devices are provided for retracting a cutting assembly in the event of a failure on a motorized electrosurgical device.

In one aspect, a surgical device is provided that includes a handle portion, an elongated shaft, a cutting assembly, a motor, a processor, and an actuator. The handle portion has the elongated shaft extending distally therefrom. The elongated shaft has first and second jaws at a distal end thereof that are configured to engage tissue therebetween. The cutting assembly is configured to move relative to the first and second jaws to cut tissue engaged between the first and second jaws. The motor is configured to drive the cutting assembly relative to the first and second jaws, and the processor is coupled to the motor and is configured to control the motor. The actuator is configured to receive an input from a user that causes power to be supplied to the motor through the processor. In an exemplary embodiment, the device has a normal mode in which the processor controls the motor to move the cutting assembly, and a bailout mode in which the processor is bypassed and power is delivered directly to the motor to cause the cutting assembly to move proximally relative to the first and second jaws.

The surgical device can vary in any number of ways. For example, the surgical device can include a switch on the handle for moving the device from the normal mode to the bailout mode. For another example, when the device is in the normal mode, a power source can be in a first position directly electrically connected to the processor, and when the device is in the bailout mode, the power source can be in a second position electrically disconnected from the processor and directly electrically connected to the motor. As another example, the power source can include a battery that mates to the handle portion in a first position in the normal mode, and that mates to the handle portion in a second position to move the device to the bailout mode.

As another example, an end cap can electrically connect the motor to the processor in the normal mode, and the end cap can be configured to electrically disconnect the motor from the processor in the bailout mode. In another example, the processor can control a speed of the motor and a direction of rotation of the motor such that the motor is configured to advance the cutting assembly distally relative to the first and second jaws, and the motor can be configured to proximally retract the cutting assembly relative to the first and second jaws.

In another aspect, a surgical device is provided that includes a handle assembly, an elongated body, a motor-driven cutting assembly, a processor, and a bailout mechanism. The handle assembly includes an actuator, and the elongated body extends distally from the handle assembly and has an end effector on the distal end thereof. The motor-driven cutting assembly is movable through the end effector so as to cut tissue engaged by the end effector. The processor is configured to control movement of the cutting assembly, and the bailout mechanism is configured to override the processor such that power can be delivered directly to the motor-driven cutting assembly.

The surgical device can vary in any number of ways. For example, the cutting assembly can be limited to moving proximally through the end effector when the bailout mechanism is activated. As another example, a power source can be directly electrically connected to the processor, and activation of the bailout mechanism can electrically disconnect the power source from the processor and can directly electrically connect the power source to the motor.

In another example, the bailout mechanism can include a removable cap that when connected electrically connects a power source to the processor, and when removed disconnects the power source from the processor. In yet another example, the processor can control a speed of a motor coupled to the cutting assembly and a direction of rotation of the motor such that the motor can be configured to advance the cutting assembly distally relative to the first and second jaws. In this example, the motor can be configured to proximally retract the cutting assembly relative to the first and second jaws.

In another aspect, a method for cutting tissue is provided that includes engaging tissue between first and second jaws on a surgical device. The method also includes actuating an actuator on a handle assembly of the surgical device to cause power to be delivered to a motor through a processor in the surgical device. The motor advances a cutting assembly through the first and second jaws to at least partially cut the tissue engaged between the first and second jaws. The method further includes actuating a bailout mechanism on the surgical device to cause power to bypass the processor and to be supplied directly to the motor. The motor causes the cutting assembly to move proximally relative to the first and second jaws.

The method can vary in any number of ways. For example, actuating a bailout mechanism can include actuating a switch on the handle to move the device between power being delivered to the motor through the processor and power bypassing the processor to be supplied directly to the motor. As another example, actuating a bailout mechanism can include removing a cap on the handle to disconnect the motor from the processor, and coupling a power source directly to the motor. As another example, actuating a bailout mechanism can include moving a power source from a first positon directly electrically connected to the processor and to a second position electrically disconnected from the processor and directly electrically connected to the motor.

For another example, the processor can control a speed of the motor and a direction of rotation of the motor such that the motor advances the cutting assembly distally relative to the first and second jaws, and the motor proximally retracts the cutting assembly relative to the first and second jaws. As another example, when the bailout mechanism is actuated and power is delivered directly to the cutting assembly, the motor can operate at a full rotational speed to cause the cutting assembly to move proximally.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 7 is a circuit diagram of internal connections of the powered surgical device of FIG. 5;

FIG. 8 is a circuit diagram of internal connections of the powered surgical device of FIG. 5;

FIG. 9 is a circuit diagram of internal connections of the powered surgical device of FIG. 5;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. To the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for retracting a cutting assembly in the event of a failure on a motorized electrosurgical device. In particular, methods and devices are provided for disconnecting power between a processor and a motor and for applying power directly to the motor on a motorized electrosurgical device.

Figure 1:
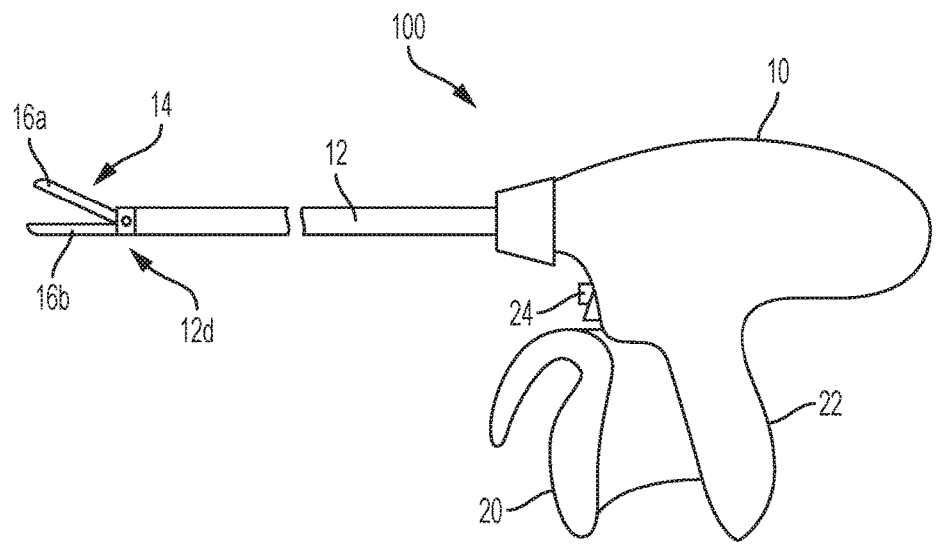
FIG. 1 is a side view illustration of one embodiment of a powered surgical device.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable toward and away from the stationary grip 22 to open and close jaws of the end effector 14. The shaft portion 12 extends distally from the proximal handle portion and has a lumen (not shown) extending therethrough for carrying mechanisms for actuating the end effector 14.

The end effector can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can be in direct contact for engaging tissue therebetween. In the illustrated embodiment, the upper jaw 16a pivots relative to the shaft portion 12 and relative to the lower jaw 16b while the lower jaw 16b remains stationary. While the illustrated jaws 16a, 16b have a substantially elongated and straight shape, a person skilled in the art will appreciate that one or both of the jaws 16a, 16b can be in various directions. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset and spaced apart from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to gears that interact with a rack disposed within the handle. Manual movement of the closure grip 20 toward the stationary grip 22 can move the rack either proximally or distally relative to the end effector 14 to either pull or push the jaws 16a, 16b closed. In other embodiments, the drive shaft can include or be coupled to a drive screw which can be moved proximally by a drive nut that is rotated by a series of gears. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as actuator 24, that can be separate from the closure actuator 20. The second actuator can be configured to advance a cutting assembly, apply energy to tissue, or both, and is referred to herein as a "firing actuator." The firing actuator 24 can have various sizes, shapes, and configurations, but in the illustrated embodiment it is in the form of a button or trigger that can be depressed by a user. In another embodiment, the firing actuator 24 can be in the form of a switch, lever, etc., that can be slid, pivoted, or otherwise moved by a user. Depressing or pivoting the actuator can activate various elements in the device, and can cause a cutting assembly to advance through the end effector and/or cause energy to be delivered to the jaws. For example, depressing or pivoting the firing actuator can cause a cutting assembly to advance distally and/or retract proximally relative to the jaws 16a, 16b. More specifically, the firing actuator can be in electrical communication with a motor disposed in the proximal handle portion 10. The motor can be operatively coupled to the cutting assembly using known components, such as one or more gears and a rack or drive screw.

Figure 2:
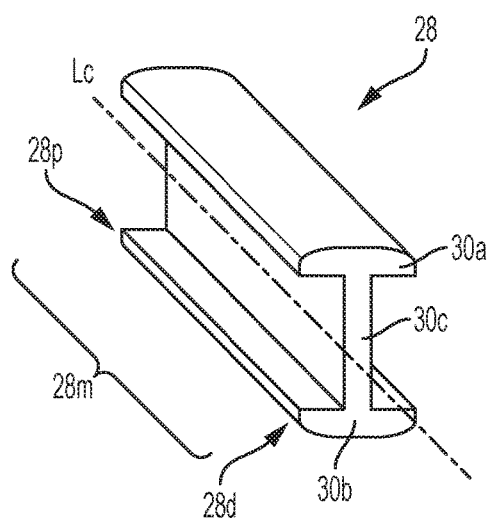
FIG. 2 is a perspective view illustration of a compression member of the powered surgical device of FIG. 1.

The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels through slots formed in each jaw to pull the jaws into a parallel orientation and to compress tissue therebetween. The compression member 28 can include a cutting element (not shown) positioned at the distal end 28d thereof and formed on a connecting portion 30c of the compression member 28. In some embodiments, the cutting element can be integrally formed with the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can include a shaft having a knife blade that is not attached to a compression member such that the cutting assembly can advance and retract relative to the jaws without applying compression to the tissue.

Figure 3:
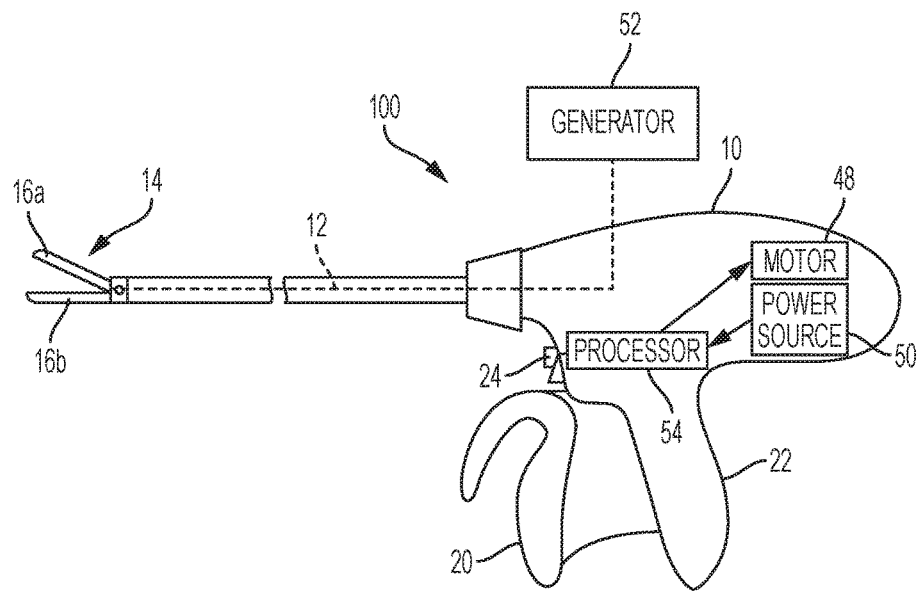
FIG. 3 is another side view illustration of the powered surgical device of FIG. 1, schematically illustrating various components in the handle of the device.

As shown in FIG. 3, the handle portion 10 of the surgical device 100 can include components for operating the device, such as a motor 48, a power source 50, a generator 52, and a processor 54, as well as various sensors (not shown). The device 100 can also include various components for delivering energy, such as radiofrequency or ultrasound energy, to tissue, and these components can be disposed at various locations in the device 100, such as in the proximal handle portion 10 and/or in the jaws 16a, 16b. The firing actuator 24 can be coupled to the processor 54, and the processor 54 can be coupled to the motor 58, the power source 50, and/or the generator 52 (as well as any sensors provided). Firing the actuator 24 sends a signal to the processor 54, which can cause the power source 50 to provide power to the motor 48 through the processor 54. The motor 48 can drive the cutting assembly, and the processor 54 can control a speed and a direction of the motor, which in turn alters a speed and a direction of the cutting assembly.

The generator 52 can be a separate unit that is electrically connected to the surgical device 100 to decrease the size and weight of the surgical device 100, and it can be operatively coupled to an actuator on the surgical device so that the device is configured to apply energy to tissue engaged by the end effector when the actuator is activated. The generator can be operably coupled to the firing actuator 24 or the generator can be coupled to a second actuator. The generator can be any suitable generator known in the art, such as an RF generator or an ultrasound generator. A lumen (not shown) of the shaft portion 12 can carry electrical leads or wires that can deliver electrical energy to components of the end effector 14. The generator 52 can be coupled to the power source 50, such as a battery disposed in the proximal handle portion 10 or it can be coupled to an external power source, such as an electrical outlet or have its own power.

Figure 4:
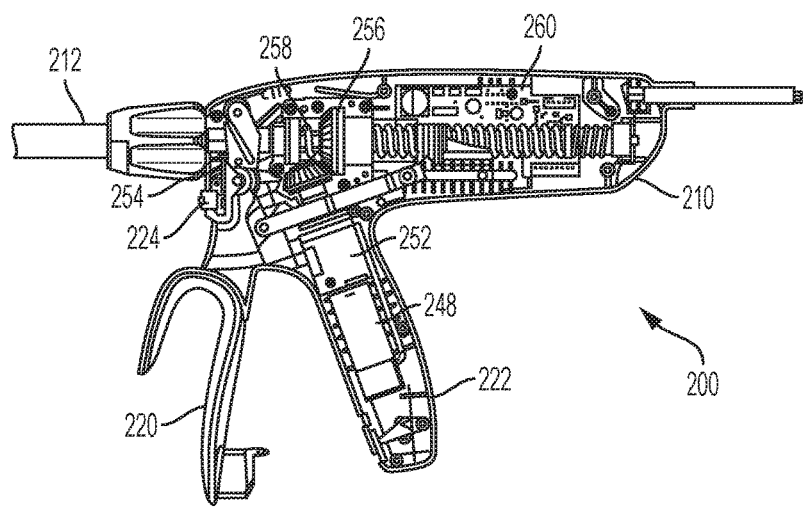
FIG. 4 is a side cutaway view of another embodiment of a powered surgical device.
Figure 5:
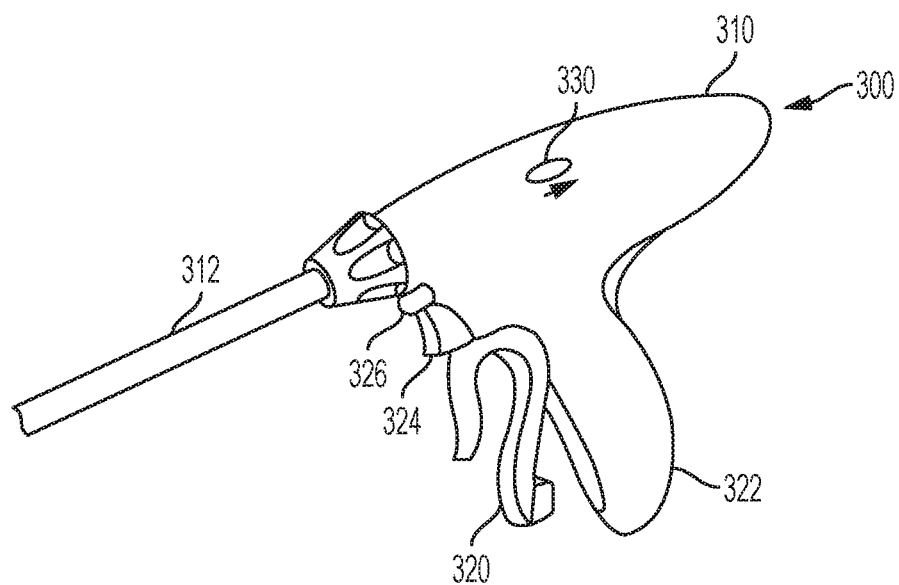
FIG. 5 is a side perspective view of another embodiment of a powered surgical device.

FIG. 4 illustrates one exemplary configuration of a surgical device 200 having components for operating the device. The surgical device 200 can generally be configured and used similar to the surgical device 100 of FIGS. 1-3. As seen in FIG. 4, the surgical device 200 has a shaft portion 212, and a proximal handle portion 210 including a closure grip 220 and a stationary grip 222. The surgical device 200 has a firing actuator 224 that is configured to advance distally and/or retract proximally a cutting assembly through an end effector (not shown) positioned on a distal end of the shaft portion 212. The firing actuator 224 is a button that can be depressed by a user. The firing actuator 224 is coupled to and in communication with a processor 260, which can include a circuit board and/or a controller. The processor 260 can be in communication with a motor 248, a power source such as a battery, and/or a generator. The motor 248 is disposed in the proximal handle portion 210, and it can be operatively coupled to a gear box 252, which is operably coupled to a motor bevel gear 254. The motor bevel gear 254 is operably coupled in turn to a drive bevel gear 256, which is operably coupled to a drive shaft 258. Activation of the firing actuator 224 can thus provide a signal to the processor 260. The processor 260 can cause power to be delivered from the power source to the motor 248, which rotates the gear box 252. The gear box 252 causes the motor bevel gear 254 to rotate, which engages with and rotates the drive bevel gear 256, which drives the drive shaft 258 distally or proximally. Upon rotation of the drive bevel gear 256, the drive shaft 258 can be driven distally or proximally through known means, such as a thread along the drive shaft 258. Distal movement of the drive shaft 258 advances the cutting assembly distally through an end effector. Proximal movement of the drive shaft 258 retracts the cutting assembly proximally from the end effector. A person skilled in the art will appreciate that the drive shaft can be advanced and retracted using a number of different techniques, such as a rack system, one or more linkages, a ball bearing and nut system, a bevel and spur gear system, etc.

As indicated above, the surgical device 200 has a generator (not shown) that is operatively coupled to an actuator on the surgical device 200 so that the device 200 is configured to apply energy to tissue engaged by the end effector when the actuator is activated. The generator can be operably coupled to the firing actuator 224 or the generator can be coupled to a second actuator. The generator can be any suitable generator known in the art, such as an RF generator or an ultrasound generator. A lumen (not shown) of the shaft portion 212 can carry electrical leads or wires that can deliver electrical energy to components of the end effector.

Under normal operation of a surgical device as described above, power can be supplied from a power source, e.g., the battery, through a processor to a motor, resulting in distal or proximal movement of a cutting assembly through an end effector positioned on a distal end of the surgical device. In particular, the processor instructs the power source to provide power to the motor. In certain instances, the surgical device may fail to successfully complete a cutting stroke, for example if the device jams during cutting because of thick tissue or if a power failure occurs. Removing the surgical device from a patient before retracting the cutting assembly may cause significant harm to the patient, though. If the surgical device malfunctions during a firing stroke, i.e., prior to full advancement and full retraction of the cutting assembly, a surgeon may be required to retract the cutting assembly from the jaws of the end effector. Accordingly, a bailout mechanism is provided that can allow retraction of the cutting assembly in the event of a malfunction.

In general, a surgical device can be provided with a handle and an elongated shaft extending distally therefrom. The elongated shaft can have an end effector at a distal end thereof, which can have first and second jaws. The jaws can be configured to engage tissue therebetween. A cutting assembly can be configured to move relative to the first and second jaws so as to cut tissue engaged between the first and second jaws. The cutting assembly can be driven distally and proximally by a motor relative to the first and second jaws. A processor, which can include a circuit board and/or a controller, can be coupled to the motor, and it can be configured to control the motor. A power source, such as a battery, can provide power to the motor through the processor. An actuator can be part of the surgical device, and it can be configured to receive an input from a user. Actuation of the actuator can cause power from the power source to be supplied to the motor through the processor to move the cutting assembly. The surgical device can have a normal mode in which the processor controls the motor to move the cutting assembly. The surgical device can also have a bailout mode in which the processor is bypassed and power is delivered directly to the motor to cause the cutting assembly to move proximally relative to the first and second jaws, retracting the cutting assembly from the first and second jaws. The first and second jaws can then open to release tissue engaged between, and a surgeon can subsequently withdraw the surgical device from a patient. The bailout mode may allow a surgeon to rapidly remove the surgical device during any emergency situation, for example if normal operation of the device malfunctions, while minimizing any harm to the patient. Electronic bailout of the cutting assembly in the form of a powered retraction of the cutting assembly from the jaws may also be fast and less prone to human error than other mechanisms, ensuring a safe retraction during a potentially high-stress situation in which the surgeon is attempting to monitor the patient and safely remove the device at the same time.

Figure 6:
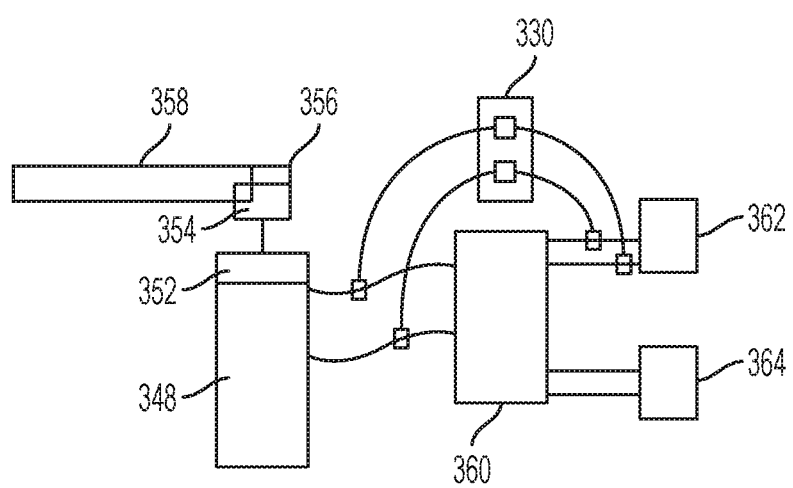
FIG. 6 is a schematic illustration of internal connections of the powered surgical device of FIG. 5.

FIGS. 5-9 illustrate one embodiment of a surgical device 300 having an electronic bailout. The surgical device 300 can generally be configured and used similar to the surgical devices 100, 200 of FIGS. 1-4. Surgical device 300 has a shaft portion 312, and a proximal handle portion 310 including a closure grip 320 and a stationary grip 322. The surgical device 300 has a firing actuator 324 that can be configured to advance distally and/or retract proximally a cutting assembly through an end effector (not shown) positioned on a distal end of the shaft portion 312. The closure grip 320 is effective to move jaws of the end effector between open and closed positions. The firing actuator 324 is in communication with a processor 360, which can include a circuit board and/or a controller, within the proximal handle portion 310. As seen in FIGS. 6-7, the processor 360 is in communication with a motor 348, a power source 362 such as a battery, and a generator 364. The motor 348 and a gear box 352 are disposed in the proximal handle portion 310. The motor 348 and the gear box 352 can be operatively coupled to a bevel gear 354 that is operably coupled to a bevel gear 356, which is operably coupled to a drive shaft 358. The processor 360 is also coupled to an energy activator 326, which, when activated, the surgical device 300 is configured to apply energy to tissue. The processor 360, the motor 348, and the gear box 352 are also electrically coupled to an electrical bailout switch 330 in the form of a button on an external surface of the proximal handle portion 310. One side of the bailout switch 330 is coupled to the connection between the power source 362 and the processor 360, and an opposite side of the bailout switch 330 is coupled to the connection between the processor 360 and the motor 348. While the bailout switch takes the form of a button in FIG. 5, the switch can take a variety of forms, such as a lever, a touch pad, etc.

When the device 300 is in a normal mode, the bailout switch 330 is in an off position and does not affect operations of the device 300. The power source 362 connects to the motor 348 through the processor 360. Actuation of the firing actuator 324 sends a signal to the processor 360, which provides power to the motor 348 from the power source 362. The motor 348 drives the gear box 352 that drives bevel gear 354 and in turn drives bevel gear 356. Bevel gear 356 can be driven directly or via one or more additional gears or other components, and rotation of the bevel gear 356 is effective to move a drive shaft 358 proximally or distally. The drive shaft 358 fully advances distally and then fully retracts proximally the cutting assembly, representing one full cutting stroke.

Upon actuation of the bailout switch 330 by a user, the device enters a bailout mode. Activation or movement of the bailout switch 330 to the "on" position directly connects the motor 348 to the power source 362, circumventing the processor 360. The bailout switch thus provides direct power from the power source 362 to the motor 348. The bailout switch 330 is wired to cause the motor 348 to proximally drive the drive shaft 358 and thereby retract the cutting assembly from the jaws. For example, the motor 348 can turn in a clockwise direction, which can advance the drive shaft 358 and the cutting assembly, while receiving positive voltage. The motor 348 can turn in a counterclockwise direction, which can retract the drive shaft 358 and the cutting assembly, while receiving negative voltage. During the normal mode, the power source 362 can be connected to the processor 360 such that the processor 360 can control the direction that the motor 348 turns (either clockwise or counterclockwise). Upon turning the bailout switch 330 "on" and entering the bailout mode, the power source 360 will be connected directly to the motor 348 such that negative voltage is applied directly to the motor 348 to force a counterclockwise turn. As seen in FIG. 8, which illustrates a simplified circuit diagram of the power source 362, the processor 360, and the motor 348 in the normal mode, the processor 360 controls power from the power source 360 applied to the motor 348 and thus controls a direction of rotation of the motor 348. In FIG. 9, which illustrates a simplified circuit diagram of the power source 362 and the motor 348 in the bailout mode, activation of the bailout switch 330 has effectively reversed polarity such that power is supplied from the power source 362 directly to the motor 348 to force a counterclockwise turn from the motor 348, which causes retraction of the cutting assembly. In other embodiments, the device can be configured so that a counterclockwise turn by the motor advances the cutting assembly and a clockwise turn by the motor retracts the cutting assembly.

The bailout switch 330 mechanically disconnects the processor 360 from the motor 348 by physically creating a connection between the motor 348 and the power source 362 in the bailout mode, as seen in FIG. 7. However, the switch can work in a variety of different ways known in the art. For example, the switch can function digitally by using a relay, transistor, etc. The switch 330 provides power directly to the motor when the switch is turned on in the bailout mode, but other variations are possible. For instance, the switch can send a signal to the processor 360 causing the processor 360 to ignore all other commands until the cutting assembly is retracted while still allowing application of power to be controlled by the processor 360. In such an embodiment, connections in the bailout mode between the motor, the processor, and the power source would be maintained (identical to connections in the normal mode).

The button of the bailout switch can be designed to lock in place once the button has been pushed by a user, keeping the switch activated until the cutting assembly returns entirely. Once the cutting assembly returns entirely, the button can be configured to unlock, which causes the switch to turn off and the device to return to the normal mode. Locking the button down can be achieved in a variety of different ways. For example, pushing the button can move an arm inside the proximal handle portion to lock the button in place. Upon full retraction of the cutting assembly, the arm can be pushed by the cutting assembly to unlock the button. The switch can also be turned on electronically and/or digitally and can be turned off again only once the device detects full retraction of the cutting assembly. The switch can also act to prevent any other functions of the device when the switch is turned on, for example preventing the application of energy to tissue, until the cutting assembly is entirely returned and the switch is turned off.

After activation of the bailout switch 330 and entering the bailout mode, the surgical device 300 can be reused by returning to the normal mode once the switch 330 is turned off. Other variations can prevent the surgical device from returning to the normal mode and being reused once the device has entered the bailout mode through turning on the switch, effectively disabling the device to ensure that a defective device is not reused in another operation. Disablement of a device can be accomplished in numerous ways, such as by preventing the switch from turning off once the switch has been turned on or through software.

Figure 10:
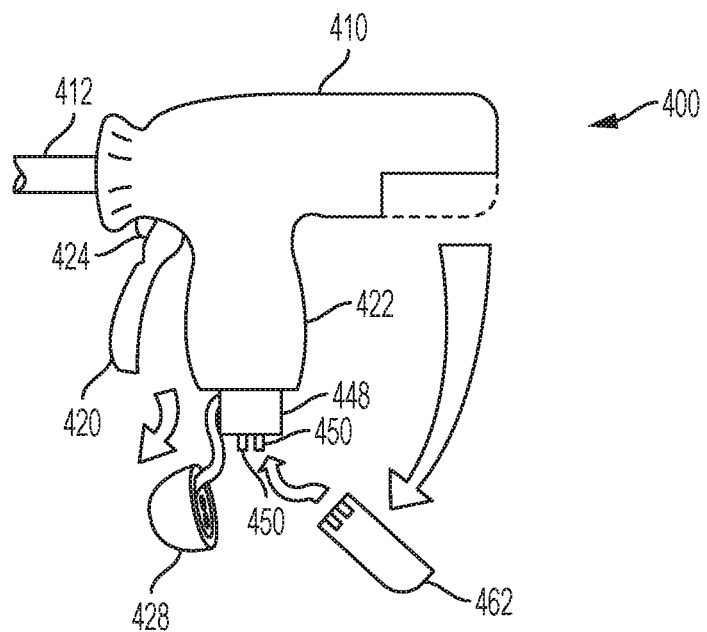
FIG. 10 is a side perspective view of another embodiment of a powered surgical device.
Figure 11:
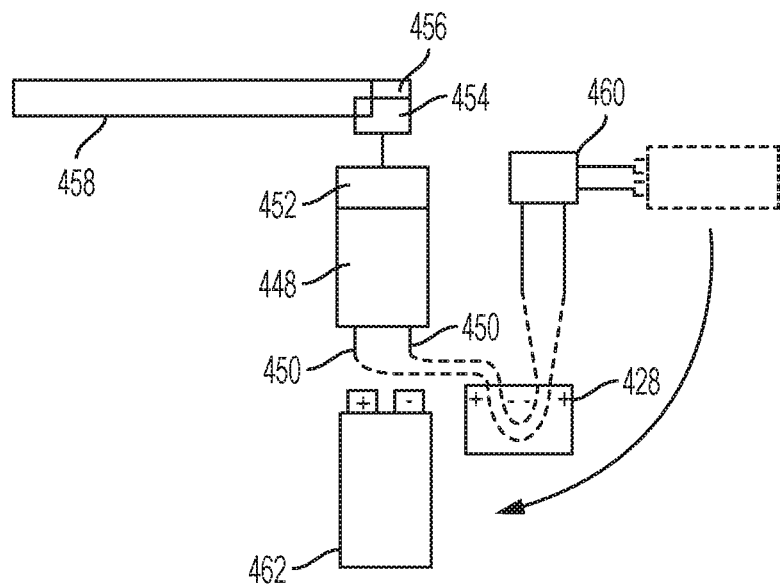
FIG. 11 is an illustration of internal connections of the powered surgical device of FIG. 10.

FIGS. 10-11 illustrate another embodiment of a surgical device having an electronic bailout. The surgical device 400 can generally be configured and used similar to the surgical devices 100, 200 of FIGS. 1-4. Surgical device 400 has a shaft portion 412 and a proximal handle portion 410 including a closure grip 420 and a stationary grip 422. The closure grip 420 is effective to move the jaws between open and closed positions. The surgical device 400 has a firing actuator 424 that can be configured to advance distally and/or retract proximally a cutting assembly through the end effector (not shown) positioned on a distal end of the shaft portion 412. The firing actuator 424 is connected to and in communication with a processor 460, which can include a circuit board and/or a controller, within the proximal handle portion 410. The processor 460 is connected to and in communication with a motor 448 and a power source 462 such as a battery. The motor 448 is operably coupled to a gear box 452 and is disposed in the proximal handle portion 410. The motor 448 and the gear box 452 can be operatively coupled to bevel gear 454 that is operably coupled (directly or indirectly) to bevel gear 456, which in turn moves a drive shaft 458 proximally or distally.

In this embodiment, a removable cap 428 covers a proximal end of the motor and gear box 448 and clips onto the proximal handle portion 410. The cap can take a variety of forms, such as a cover, a panel, etc. A connection, for example formed by electrical wires, connects the motor 448 to the processor 460 and runs through the cap 428, as seen in FIG. 11. The cap 428 is configured such that, upon removal of the cap 428 from the surgical device 400, the connection between the motor 448 and the processor 460 is broken. When the cap 428 is removed, terminals 450 on a proximal end of the motor 448 are exposed. The power source 462, such as a removable battery, is located on the proximal handle portion 410 and clips to the proximal handle portion 410. The power source 462 is configured to be detachable from a rear-end of the proximal handle portion and attachable to the terminals 450 of the motor 448. Alignment features on the motor 448 and/or the power source 462 can act to ensure a secure electrical connection is made between the motor 448 and the power source 462.

While the device 400 is in a normal mode, the cap 428 is in place and the connections between the processor 460 and the motor 448 and between the processor 460 and the power source 462 are maintained. The power source 462 connects to the motor 448 through the processor 460. Actuation of the firing actuator 424 sends a signal from the firing actuator 424 to the processor 360. Upon receipt of the signal, the processor 460 provides power to the motor 448 from the power source 462. The motor 448 drives the gear box 452, which drives the bevel gear 454, in turn driving the bevel gear 456 that drives the drive shaft 458. The drive shaft 458 fully advances distally and then fully retracts proximally the cutting assembly, representing one full cutting stroke.

Upon removal of the cap 428 from the surgical device 400 by a user, the device enters a bailout mode. The connection between the motor 448 and the processor 460 is terminated upon removal of the cap 428. If a user activates the firing trigger 424 when the device 400 is in the bailout mode, the motor 448 will not receive a signal from the processor 460. When the cap 428 is removed, the terminals 450 on the motor 448 are exposed. The power source 462 can be detached from the proximal handle portion 410, terminating the connection between the processor 460 and the power source 462, and the power source 462 can be brought into direct contact with the terminals 450 of the motor 448. The power source 462 thus can connect directly to the motor 448 and can provide direct power to the motor 448. Upon contact between the power source 462 and the terminals 450 of the motor 448, the motor 448 is driven to retract the cutting assembly.

The alignment features on the motor 448 and/or the power source 462 can cause the power source 462 to only be able to connect to the terminals 450 of the motor 448 in a configuration that drives the motor 448 to drive the drive shaft 458 in reverse and retract the cutting assembly. For example, the motor 448 can turn in a clockwise direction, which can advance the drive shaft 458 and the cutting assembly, while receiving positive voltage. The motor 448 can turn in a counterclockwise direction, which can retract the drive shaft 458 and the cutting assembly, while receiving negative voltage. During the normal mode, the power source 462 can be connected to the processor 460 such that the processor 460 can control a direction that the motor 448 turns (either clockwise or counterclockwise). Upon removing the cap 428 from the surgical device 400 and entering the bailout mode, the alignment features can be configured to allow the power source 460 to only be connected to the terminals 450 of the motor 448 to cause negative voltage to be applied directly to the terminals 450 of the motor 448 and to force a counterclockwise turn of the motor 448. In other embodiments, the device can be configured so that a counterclockwise turn by the motor advances the cutting assembly and a clockwise turn by the motor retracts the cutting assembly.

The drive shaft 458 continues to retract the cutting assembly as long as the power source 462 is applied to the terminals 450 on the motor 448. However, alternate embodiments are possible. For example, once the power source 462 contacts the terminals 450 of the motor 448, the cutting assembly can retract fully and then stop and/or the surgical device 400 can have hard stops along the proximal handle portion 410 that physically contact the cutting assembly and prevent continued retraction.

While the terminals of the motor 448 are shown as prongs, any known configuration can be used, for example concentric circles that can allow the power source 462 to be connected at any angle. Moreover, while the illustrated embodiment utilizes the power source 462 from the surgical device 400 to directly drive the motor in the bailout mode, any power source can be used. For example, if the surgical device 400 malfunctions because the power source 462 is faulty, another power source can be used in the same way as the power source 462 would have been used to reverse the motor 448.

While the connection between the motor 448 and the processor 460 is physically broken in the bailout mode in this illustrative embodiment when the cap 428 is removed, other embodiments can prevent the processor 460 from sending contradictory signals upon removal of the cap 428 in a variety of different ways, for example by software detecting removal of the cap 428 and sending a signal to the processor 460 causing the processor 460 to ignore all other commands. In such an embodiment, the cap would not be required to create and/or maintain the connection between the processor and the motor. Thus removal of the cap would not terminate the connection between the processor and the motor.

After removal of the cap 428 and the power source 462 in the bailout mode, the surgical device 400 can be reused by returning the cap 428 and the power source 462 to their original orientations, which would return the device 400 to the normal mode. Other embodiments can prevent the surgical device from being reused once the cap and/or the power source are removed, effectively disabling the device and preventing a return to the normal mode to ensure that a defective device is not reused in another operation. Disablement of a device can be accomplished in numerous ways, such as by preventing the cap and/or the power source from clipping back onto the surgical device once removed or through software.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a handle portion having an elongated shaft extending distally therefrom, the elongated shaft having first and second jaws at a distal end thereof, the jaws being configured to engage tissue therebetween;
a cutting assembly configured to move relative to the first and second jaws so as to cut tissue engaged between the first and second jaws;
a motor configured to drive the cutting assembly relative to the first and second jaws;
a processor coupled to the motor and configured to control the motor; and
an actuator configured to receive an input from a user that causes power to be supplied to the motor through the processor to move the cutting assembly relative to the first and second jaws;
wherein the device has a normal mode in which the processor controls the motor to move the cutting assembly; and the device has a bailout mode in which the processor is bypassed and power is delivered directly to the motor to cause the cutting assembly to move proximally relative to the first and second jaws.

2. The device of claim 1, further comprising a switch on the handle for moving the device from the normal mode to the bailout mode.

3. The device of claim 1, wherein, when the device is in the normal mode, a power source is in a first position directly electrically connected to the processor, and when the device is in the bailout mode, the power source is in a second position electrically disconnected from the processor and directly electrically connected to the motor.

4. The device of claim 3, wherein the power source comprises a battery that mates to the handle portion in a first position in the normal mode, and that mates to the handle portion in a second position to move the device to the bailout mode.

5. The device of claim 1, further comprising an end cap that electrically connects the motor to the processor in the normal mode, and the end cap being configured to electrically disconnect the motor from the processor in the bailout mode.

6. The device of claim 1, wherein the processor controls a speed of the motor and a direction of rotation of the motor such that the motor is configured to advance the cutting assembly distally relative to the first and second jaws, and the motor is configured to proximally retract the cutting assembly relative to the first and second jaws.

7. A surgical device, comprising:
a handle assembly including an actuator;
an elongated body extending distally from the handle assembly and having an end effector on the distal end thereof;
a motor-driven cutting assembly movable through the end effector so as to cut tissue engaged by the end effector;
a processor configured to control movement of the cutting assembly; and
a bailout mechanism configured to override the processor such that power can be delivered directly to the motor-driven cutting assembly.

8. The surgical device of claim 7, wherein the cutting assembly is limited to moving proximally through the end effector when the bailout mechanism is activated.

9. The surgical device of claim 7, wherein a power source is directly electrically connected to the processor, and activation of the bailout mechanism electrically disconnects the power source from the processor and directly electrically connects the power source to the motor.

10. The surgical device of claim 7, wherein the bailout mechanism comprises a removable cap that when connected electrically connects a power source to the processor, and when removed disconnects the power source from the processor.

11. The surgical device of claim 10, wherein, when the cap is removed, the motor is configured to be directly electrically connected to the power source.

12. The surgical device of claim 7, wherein the processor controls a speed of a motor coupled to the cutting assembly and a direction of rotation of the motor such that the motor is configured to advance the cutting assembly distally relative to the first and second jaws, and the motor is configured to proximally retract the cutting assembly relative to the first and second jaws.

13. A method for cutting tissue, comprising:
engaging tissue between first and second jaws on a surgical device;
actuating an actuator on a handle assembly of the surgical device to cause power to be delivered to a motor through a processor in the surgical device, the motor advancing a cutting assembly through the first and second jaws to at least partially cut the tissue engaged between the first and second jaws; and
actuating a bailout mechanism on the surgical device to cause power to bypass the processor and to be supplied directly to the motor to cause the cutting assembly to move proximally relative to the first and second jaws.

14. The method for cutting tissue of claim 13, wherein actuating a bailout mechanism includes actuating a switch on the handle to move the device between power being delivered to the motor through the processor and power bypassing the processor to be supplied directly to the motor.

15. The method for cutting tissue of claim 13, wherein actuating a bailout mechanism comprises removing a cap on the handle to disconnect the motor from the processor, and coupling a power source directly to the motor.

16. The method for cutting tissue of claim 13, wherein actuating a bailout mechanism comprises moving a power source from a first positon directly electrically connected to the processor and to a second position electrically disconnected from the processor and directly electrically connected to the motor.

17. The method for cutting tissue of claim 13, wherein the processor controls a speed of the motor and a direction of rotation of the motor such that the motor advances the cutting assembly distally relative to the first and second jaws, and the motor proximally retracts the cutting assembly relative to the first and second jaws.

18. The method for cutting tissue of claim 13, wherein, when the bailout mechanism is actuated and power is delivered directly to the cutting assembly, the motor operates at a full rotational speed to cause the cutting assembly to move proximally.

* * * * *